US012685675B2

(12) United States Patent
Takeda et al.

(10) Patent No.: US 12,685,675 B2
(45) Date of Patent: Jul. 21, 2026

(54) ABSORBENT PRODUCT

(71) Applicant: LIVEDO CORPORATION, Ehime (JP)

(72) Inventors: Shingo Takeda, Tokushima (JP); Yuki Takahashi, Tokushima (JP); Junki Fukumoto, Tokushima (JP); Wataru Tachibori, Tokushima (JP)

(73) Assignee: LIVEDO CORPORATION, Ehime (JP)

( * ) Notice: Subject to any disclaimer, the term of this patent is extended or adjusted under 35 U.S.C. 154(b) by 567 days.

(21) Appl. No.: 17/979,236

(22) Filed: Nov. 2, 2022

(65) Prior Publication Data

US 2023/0201045 A1    Jun. 29, 2023

(30) Foreign Application Priority Data

Dec. 28, 2021    (JP) ................................. 2021-214290

(51) Int. Cl.
*A61F 13/15*        (2006.01)

(52) U.S. Cl.
CPC ...... *A61F 13/15* (2013.01); *A61F 2013/1556* (2013.01)

(58) Field of Classification Search
CPC .. A61F 2013/15447; A61F 2013/15406; A61F 13/47; A61F 13/49; A61F 13/539;
(Continued)

(56) References Cited

U.S. PATENT DOCUMENTS

| | | | | |
|---|---|---|---|---|
| 4,381,783 A | * | 5/1983 | Elias ...................... | A61F 13/535 604/378 |
| 4,676,784 A | * | 6/1987 | Erdman ................ | A61F 13/532 604/368 |

(Continued)

FOREIGN PATENT DOCUMENTS

| | | |
|---|---|---|
| JP | 2009-22670 | 2/2009 |
| JP | 2009-72421 | 4/2009 |

(Continued)

OTHER PUBLICATIONS

Decision of Refusal issued Sep. 18, 2025 in corresponding Japanese Patent Application No. 2021-214290, with English translation (5 pages).

(Continued)

*Primary Examiner* — Rebecca E Eisenberg
*Assistant Examiner* — Ted Yang
(74) *Attorney, Agent, or Firm* — Wenderoth, Lind & Ponack, L.L.P.

(57)        ABSTRACT

In an absorbent product, an absorbent core includes an upper absorber including a super absorbent material fixedly attached between upper and lower absorber sheets. The upper absorber includes material existence regions that are arranged in the width direction and to which the super absorbent material is fixedly attached, and a material non-existence region in which the super absorbent material does not exist is arranged between each pair of adjacent material existence regions. In each material non-existence region, the upper and lower absorber sheets are entirely joined together. In at least one material non-existence region, the top sheet and the upper absorber sheet are partly joined together. The load applied when the nonwoven fabric of the top sheet is stretched 3% in the width direction is twice or more of the (Continued)

load applied when the nonwoven fabric of the upper absorber sheet is stretched 3% in the width direction.

7 Claims, 6 Drawing Sheets

(58) Field of Classification Search
CPC .............. A61F 13/5323; A61F 13/4751; A61F 13/4756; A61F 2013/530262; A61F 2013/530437; A61F 2013/53051; A61F 2013/530532; A61F 13/535; A61F 13/536; A61F 13/53752
See application file for complete search history.

(56) References Cited

U.S. PATENT DOCUMENTS

| RE32,957 E | * | 6/1989 | Elias ...................... A61L 15/18 604/378 |
| 4,840,692 A | * | 6/1989 | Kamstrup-Larsen ........................ A61F 5/4401 156/252 |
| 4,935,021 A | * | 6/1990 | Huffman ............... A61F 13/539 604/385.26 |
| 5,364,382 A | * | 11/1994 | Latimer .............. A61F 13/5376 604/378 |
| 5,788,684 A | * | 8/1998 | Abuto .............. A61F 13/53713 604/378 |
| 5,830,202 A | * | 11/1998 | Bogdanski ......... A61F 13/5323 604/378 |
| 5,964,743 A | * | 10/1999 | Abuto ................ A61F 13/5323 604/385.01 |
| 6,218,593 B1 | * | 4/2001 | Torimae .............. A61F 13/5148 604/366 |
| 6,383,431 B1 | * | 5/2002 | Dobrin .................... B29C 55/14 156/324 |
| 6,432,094 B1 | * | 8/2002 | Fujioka ................ A61F 13/494 604/385.101 |
| 6,646,179 B1 | * | 11/2003 | Melius .............. A61F 13/15203 604/368 |
| 6,673,982 B1 | * | 1/2004 | Chen ................ A61F 13/53743 604/385.101 |
| 6,965,058 B1 | * | 11/2005 | Raidel .................... A61L 15/60 604/367 |
| 7,767,878 B2 | * | 8/2010 | Suzuki .................. A61F 13/535 604/374 |
| 2001/0008675 A1 | * | 7/2001 | Meece ................ D04H 1/4291 442/361 |
| 2001/0014797 A1 | * | 8/2001 | Suzuki .............. A61F 13/15252 604/366 |
| 2004/0243078 A1 | * | 12/2004 | Guidotti ............ A61F 13/15203 604/378 |
| 2006/0081348 A1 | * | 4/2006 | Graef .................. A61F 13/5323 604/385.01 |
| 2006/0206090 A1 | * | 9/2006 | Mori .................... A61F 13/4942 604/385.28 |
| 2006/0278335 A1 | * | 12/2006 | Moriura .............. A61F 13/5323 156/279 |
| 2007/0093164 A1 | * | 4/2007 | Nakaoka ............... A61F 13/536 442/385 |
| 2007/0179469 A1 | * | 8/2007 | Takahashi ............. A61F 13/535 604/385.101 |
| 2008/0004582 A1 | * | 1/2008 | Lodge .................... A61F 13/64 604/385.01 |
| 2009/0043273 A1 | * | 2/2009 | Carlucci ............ A61F 13/5323 604/370 |
| 2009/0270825 A1 | * | 10/2009 | Wciorka ............... A61F 13/539 604/378 |
| 2009/0270826 A1 | * | 10/2009 | Schafer .............. A61F 13/5323 604/367 |
| 2010/0262099 A1 | * | 10/2010 | Klofta .................. A61F 13/539 604/361 |
| 2010/0262108 A1 | * | 10/2010 | Kawazoe ............... A61F 13/15 604/385.01 |
| 2011/0060303 A1 | * | 3/2011 | Bissah .............. A61F 13/53756 604/374 |
| 2011/0152809 A1 | * | 6/2011 | Carlucci ............. A61F 13/5323 428/206 |
| 2011/0208147 A1 | * | 8/2011 | Kawakami .......... A61F 13/5323 604/385.01 |
| 2011/0313384 A1 | * | 12/2011 | Akiyama ............ A61F 13/5323 604/378 |
| 2012/0228180 A1 | * | 9/2012 | Urushihara ....... A61F 13/55145 604/372 |
| 2013/0079740 A1 | * | 3/2013 | Ehrnsperger ............ A61L 15/58 604/367 |
| 2013/0226120 A1 | * | 8/2013 | Van De Maele ..... B32B 29/005 428/206 |
| 2013/0245589 A1 | * | 9/2013 | Toda .................. A61F 13/53747 604/378 |
| 2014/0163501 A1 | * | 6/2014 | Ehrnsperger .......... A61F 13/539 604/374 |
| 2014/0163503 A1 | * | 6/2014 | Arizti .................. A61F 13/5323 604/374 |
| 2014/0257220 A1 | * | 9/2014 | Neton .................... B32B 27/08 604/385.01 |
| 2014/0336606 A1 | * | 11/2014 | Bewick-Sonntag ........................ A61F 13/538 604/378 |
| 2014/0371701 A1 | * | 12/2014 | Bianchi ............ A61F 13/53743 604/378 |
| 2015/0080837 A1 | * | 3/2015 | Rosati ..................... A61F 13/84 604/385.101 |
| 2015/0196436 A1 | * | 7/2015 | Hishikawa ............ A61F 13/539 604/374 |
| 2015/0209197 A1 | * | 7/2015 | Ota ........................ A61F 13/537 604/372 |
| 2015/0224000 A1 | * | 8/2015 | Ota ........................ A61F 13/15 604/373 |
| 2015/0250664 A1 | * | 9/2015 | Uda .................... A61F 13/4756 604/370 |
| 2015/0359687 A1 | * | 12/2015 | Goda .................... A61F 13/539 156/60 |
| 2016/0158075 A1 | * | 6/2016 | Sheldon ............... A61F 13/534 604/382 |
| 2016/0199527 A1 | * | 7/2016 | Ota ........................ A61L 15/26 502/402 |
| 2016/0235595 A1 | * | 8/2016 | Ehrnsperger .......... A61F 13/536 |
| 2016/0278998 A1 | * | 9/2016 | Takahashi .......... B29C 66/0324 |
| 2016/0361206 A1 | * | 12/2016 | Engelhardt .............. B32B 5/02 |
| 2017/0135870 A1 | * | 5/2017 | Kamphus ............ A61F 13/5323 |
| 2017/0165396 A1 | * | 6/2017 | Turner ................. A61F 13/514 |
| 2017/0209616 A1 | * | 7/2017 | Turner ............... A61F 13/5323 |
| 2017/0360983 A1 | * | 12/2017 | Maldonado ....... A61F 13/51458 |
| 2018/0021168 A1 | * | 1/2018 | Isaac .................... A61F 13/539 604/375 |
| 2018/0064583 A1 | * | 3/2018 | Van De Maele ......... B32B 5/18 |
| 2018/0168882 A1 | * | 6/2018 | van der Klugt ........ B32B 37/12 |
| 2018/0222171 A1 | * | 8/2018 | Degroot ................ B32B 5/022 |
| 2018/0263831 A1 | * | 9/2018 | Manabe ............... A61F 13/534 |
| 2018/0344542 A1 | * | 12/2018 | Takahashi ............ A61F 13/515 |
| 2019/0201251 A1 | * | 7/2019 | Rosati ..................... A61F 13/45 |
| 2020/0008987 A1 | * | 1/2020 | Suyama ................ A61F 13/535 |
| 2020/0107972 A1 | * | 4/2020 | Raycheck ......... A61F 13/55105 |
| 2020/0214362 A1 | * | 7/2020 | Sakai .................. A61F 13/4902 |
| 2020/0214363 A1 | * | 7/2020 | Sakai ...................... B29C 66/21 |
| 2020/0214903 A1 | * | 7/2020 | Urakawa ............... A61F 13/496 |
| 2020/0214904 A1 | * | 7/2020 | Tsunoda ................... B32B 7/03 |
| 2020/0214905 A1 | * | 7/2020 | Sakai ...................... B29C 66/41 |
| 2020/0368076 A1 | * | 11/2020 | Knittle .............. G06K 19/0722 |
| 2020/0375814 A1 | * | 12/2020 | Tsunoda ................. B32B 33/00 |
| 2021/0059875 A1 | * | 3/2021 | Koyama ............... A61F 13/511 |
| 2021/0093489 A1 | * | 4/2021 | Manabe ............... A61F 13/536 |
| 2021/0228424 A1 | * | 7/2021 | Tsunoda ................ B29C 66/727 |
| 2021/0267822 A1 | * | 9/2021 | Nakamura ........... A61F 13/539 |
| 2021/0338494 A1 | * | 11/2021 | Hasezawa ............... A61F 13/56 |
| 2021/0378885 A1 | * | 12/2021 | Greening, II .......... A61F 13/84 |
| 2022/0023116 A1 | * | 1/2022 | Schuberth ............ A61F 13/536 |
| 2022/0031527 A1 | * | 2/2022 | Bianchi .................. A61F 13/45 |

(56) References Cited

U.S. PATENT DOCUMENTS

| | | | | | |
|---|---|---|---|---|---|
| 2022/0031528 A1 * | 2/2022 | Grenier | ................. | A61F 13/536 | |
| 2022/0031534 A1 * | 2/2022 | Bianchi | .............. | A61F 13/5622 | |
| 2023/0081440 A1 * | 3/2023 | Roets | ................. | A61F 13/5323 | |
| | | | | 604/385.01 | |
| 2023/0111494 A1 * | 4/2023 | Lambertz | ......... | A61F 13/15707 | |
| | | | | 604/374 | |
| 2024/0139043 A1 * | 5/2024 | Jeong | ................... | A61F 13/539 | |
| 2024/0173176 A1 * | 5/2024 | Kishida | ............ | A61F 13/49011 | |
| 2024/0216186 A1 * | 7/2024 | Bäck | ....................... | A61F 13/49 | |
| 2024/0383226 A1 * | 11/2024 | Musha | ..................... | B32B 7/14 | |

FOREIGN PATENT DOCUMENTS

| | | | | | |
|---|---|---|---|---|---|
| JP | 4416441 | | 2/2010 | | |
| JP | 4442820 | B2 * | 3/2010 | | |
| JP | 4502586 | | 7/2010 | | |
| JP | 2011-125360 | | 6/2011 | | |
| JP | 2011-135921 | | 7/2011 | | |
| JP | 2012-120707 | | 6/2012 | | |
| JP | 2015-202394 | | 11/2015 | | |
| JP | 6353237 | | 7/2018 | | |
| JP | 2020-81432 | | 6/2020 | | |
| WO | WO-2011102125 A1 * | | 8/2011 | ........... | A61F 13/531 |

OTHER PUBLICATIONS

Office Action issued May 22, 2025 in Japanese Patent Application No. 2021-214290, with English Translation.

* cited by examiner

ABSORBENT PRODUCT

CROSS REFERENCE TO RELATED APPLICATIONS

The present application claims the benefit of priority to Japanese Patent Application No. 2021-214290 filed on Dec. 28, 2021, the contents of which are incorporated herein by reference in its entirety.

TECHNICAL FIELD

The present invention relates to an absorbent product.

BACKGROUND ART

Absorbent products such as disposable diapers are conventionally used. Such absorbent products achieve, for example, an improvement in the amount of absorption by arranging an absorbent core including a super absorbent material on a portion where body waste such as urine is received from a wearer. For example, the absorbent product disclosed in Japanese Patent Publication No. 4502586 (Document 1) includes an absorbent pad (absorbent core) that includes a sheet-like absorbent layer containing absorbent resin powder and a fiber assembly layer containing pulp fiber. In the sheet-like absorbent layer, the absorbent resin powder is contained between a plurality of nonwoven fabric sheets. The sheet-like absorbent layer includes absorbent-resin-powder existence regions and absorbent-resin-powder non-existence regions. In the absorbent-resin-powder non-existence regions, the nonwoven fabric sheets are joined together to form a sealed parts. According to Document 1, when the absorbent resin absorbs body fluids and swells, air gaps are formed between the fiber assembly layer and the sealed parts. This allows the body fluids seeping out through the fiber assembly layer to be diffused through the air gaps, and accordingly prevents the return of the body fluids (fluid return).

In the absorbent product disclosed in Japanese Patent Application Laid-Open No. 2009-72421 (Document 2), an absorber containing fibrous matter includes a plurality of regions that are provided with an absorbent polymer and arranged in a plane direction with clearance therebetween. When the absorbent polymer absorbs urine, the regions provided with the absorbent polymer increase in thickness and the surface of the absorber becomes uneven. This produces a space between the absorber and a top sheet, resulting in an improvement in air permeability. In the disposable diaper disclosed in Japanese Patent Application Laid-Open No. 2011-135921 (Document 3), an absorber includes a large number of small absorptive portions arranged in length and breadth directions. The disposal diaper further includes a crepe sheet arranged on the skin abutment surface side of the small absorptive portions so as to be overlapped with a top sheet in approximately parallel. Body fluids that are discharged permeate through the top sheet and reach the crepe sheet, and the crepe sheet covers the small absorptive portions and becomes embedded in valleys between the small absorptive portions to form valley paths. The presence of the valley paths allows the passage of the discharged body fluids.

Japanese Patent Publication No. 6353237 (Document 4) discloses that, in an absorber that includes an absorbent resin between upper and lower sheets but does not include pulp fiber, stretching stress applied when the lower sheet is stretched 5% is 20% or higher and 75% or lower of stretching stress applied when the upper sheet is stretched 5%. Accordingly, the absorber can bulge downward more easily than upward, and this reduces the occurrence of large unevenness in the surface of the absorber on the wearer side.

As described previously, the absorbent product according to Document 1 improves liquid diffusion properties and suppresses fluid return by the presence of the air gaps between the fiber assembly layer and the sealed parts, but this is not always sufficient. There is thus demand for new techniques capable of improving liquid diffusion properties and suppressing fluid return.

SUMMARY OF THE INVENTION

The present invention is intended for an absorbent product that receives body waste from a wearer, and it is an object of the present invention to improve liquid diffusion properties and suppress fluid return.

An absorbent product according to the present invention includes a liquid-pervious top sheet, a water-repellent or liquid-impervious back sheet, and an absorbent core disposed between the top sheet and the back sheet and extending in a longitudinal direction. The absorbent core includes an upper absorber including a super absorbent material fixedly attached between an upper absorber sheet and a lower absorber sheet, and a lower absorber including a sheet-like fiber assembly and disposed between the upper absorber and the back sheet. The upper absorber includes a plurality of material existence regions that are arranged in a width direction with clearance therebetween and to which the super absorbent material is fixedly attached, and a material non-existence region in which the super absorbent material does not exist is arranged between each pair of the plurality of material existence regions that are adjacent to each other in the width direction. In each material non-existence region, the upper absorber sheet and the lower absorber sheet are entirely joined together to form a first joined portion. In at least one material non-existence region, the top sheet and the upper absorber sheet are partly joined together to form a second joined portion. A load applied when nonwoven fabric of the top sheet is stretched 3% in the width direction is twice or more of a load applied when nonwoven fabric of the upper absorber sheet is stretched 3% in the width direction.

According to the present invention, it is possible to improve liquid diffusion properties and suppress fluid return.

Preferably, the nonwoven fabric of the top sheet may have higher tensile strength in the width direction than the nonwoven fabric of the upper absorber sheet.

Preferably, fineness of the nonwoven fabric of the top sheet may be 1.1 times or more of fineness of the nonwoven fabric of the upper absorber sheet.

Preferably, a basis weight of the nonwoven fabric of the top sheet may be 1.1 times or more of a basis weight of the nonwoven fabric of the upper absorber sheet.

Preferably, in a material non-existence region including the second joined portion, a joint region in which the top sheet and the upper absorber sheet are joined together may have an area ratio higher than or equal to 1% and lower than or equal to 50%.

Preferably, the second joined portion has lower peel strength than the first joined portion.

These and other objects, features, aspects and advantages of the present invention will become more apparent from the following detailed description of the present invention when taken in conjunction with the accompanying drawings.

DETAILED DESCRIPTION

Figure 1:
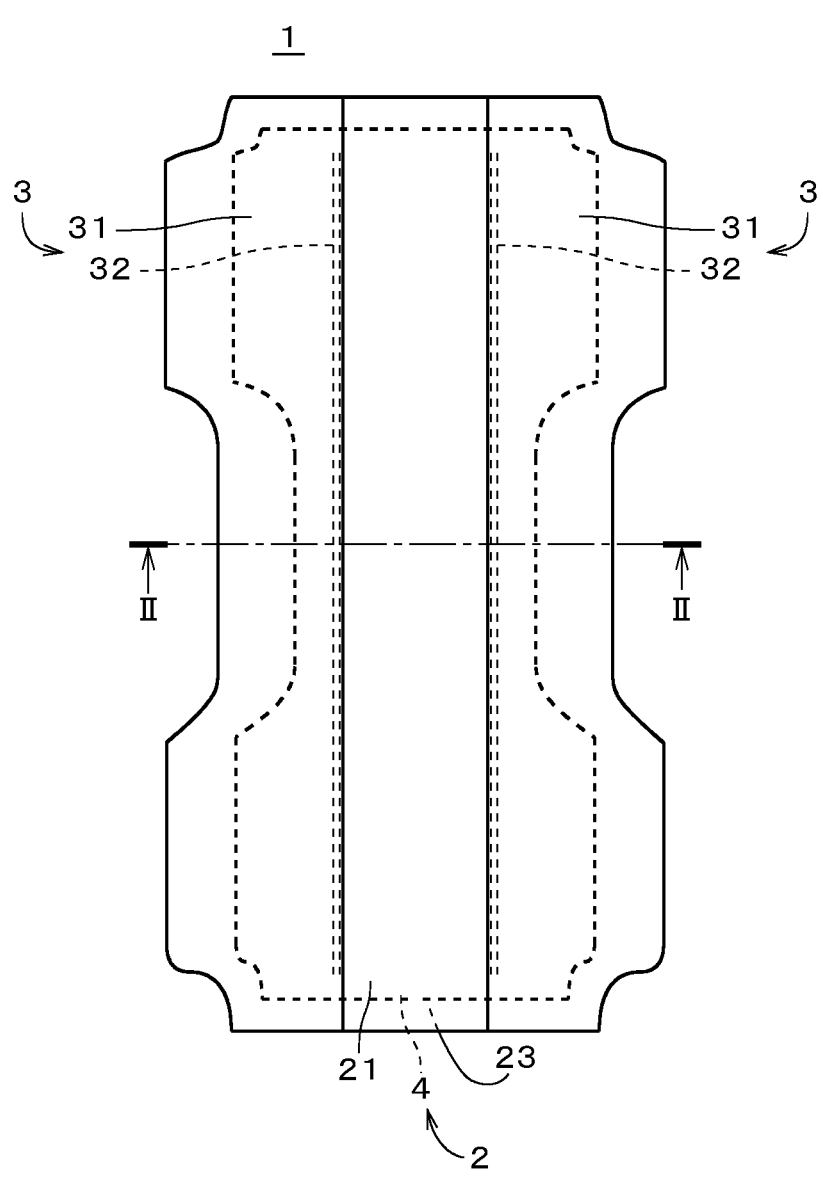
FIG. 1 is a plan view of an absorbent product.

FIG. 1 is a plan view illustrating an absorbent product 1 when laid out flat according to one embodiment of the present invention. The absorbent product 1 is an auxiliary absorbent pad that is attached to the inner side (i.e., wearer side) of an exterior product such as a disposable diaper worn by a wearer, to receive body waste such as urine from the wearer. In FIG. 1, the absorbent product 1 is illustrated with the surface on the side that comes in contact with a wearer when the product is worn being illustrated at the near side.

Figure 2:
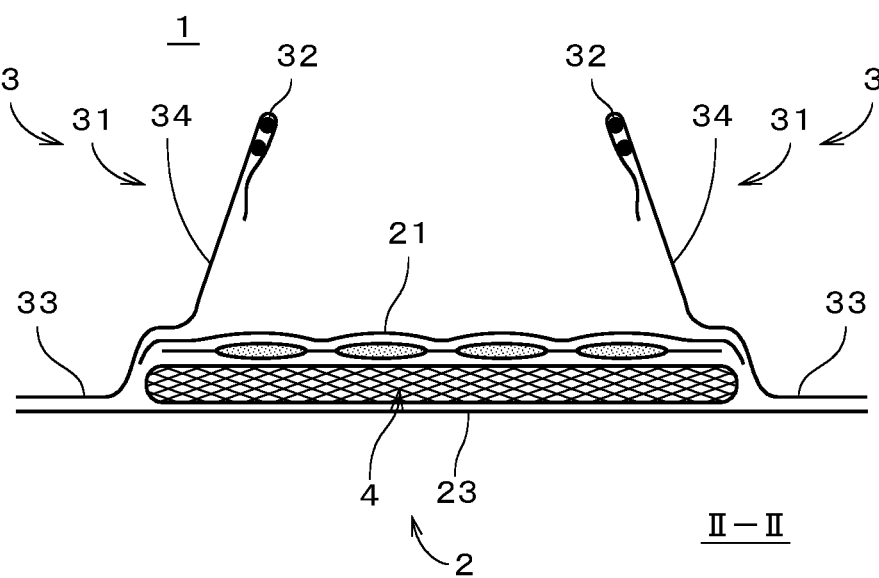
FIG. 2 is a sectional view of the absorbent product.

FIG. 2 is a sectional view of the absorbent product 1 taken along a plane perpendicular to the longitudinal direction (i.e., up-down direction in FIG. 1) at a position II-II illustrated in FIG. 1. As illustrated in FIGS. 1 and 2, the absorbent product 1 includes an approximately sheet-like main body part 2 and a pair of side sheets 3. The main body part 2 includes a liquid-pervious top sheet 21, a water-repellent or liquid-impervious back sheet 23, and an approximately sheet-like absorbent core 4 arranged between the top sheet 21 and the back sheet 23. For the convenience of illustration, each component of the absorbent product 1 is illustrated apart from each other in the thickness direction in FIG. 2. The contour of the absorbent core 4 is illustrated by a thick broken line in FIG. 1 in order to facilitate understanding of the drawing.

As illustrated in FIG. 1, the absorbent core 4 and the main body part 2 have approximately rectangular shapes extending in the longitudinal direction in plan view. To be more specific, the absorbent core 4 and the main body part 2 each have a so-called hourglass shape whose both end portions in the longitudinal direction are greater in width than the central portion. The outside shape of the absorbent core 4 corresponds to the outside shape of a lower absorber 46, which will be described later. The main body part 2 is one size larger than the absorbent core 4, so that the entire absorbent core 4 is located inside the outer peripheral edge of the main body part 2. The outside shape of the main body part 2 corresponds to the outside shape of the back sheet 23, and the length of the back sheet 23 in the longitudinal direction and width thereof in the width direction are greater than the length and width of the absorbent core 4. As illustrated in FIG. 2, the top sheet 21 covers one main surface of the absorbent core 4 on the wearer side. The back sheet 23 covers the other main surface of the absorbent core 4, i.e., the main surface on the opposite side to the wearer. In the present embodiment, the top sheet 21 has an approximately rectangular shape (see FIG. 3, which will be described later) and is joined to the back sheet 23 with a hot-melt adhesive or the like outside the absorbent core 4 in the longitudinal direction.

The top sheet 21 is a liquid-pervious sheet member that quickly catches moisture in body waste discharged from the wearer and transfers the moisture to the absorbent core 4. The absorbent core 4 absorbs moisture that has permeated through the top sheet 21, and quickly traps the moisture. The back sheet 23 prevents moisture or the like in the body waste that has reached the back sheet 23 from seeping out to the outside of the main body part 2. The details of the structure of the absorbent core 4 will be described later.

As illustrated in FIGS. 1 and 2, the pair of side sheets 3 is arranged on both side portions of the main body part 2 (i.e., both sides in the width direction perpendicular to the longitudinal direction) and extends approximately along the entire length of the main body part 2 in the longitudinal direction. Each side sheet 3 includes a side-sheet main body 31 and a side-wall elastic member 32. As illustrated in FIG. 2, the side-sheet main body 31 includes a fixed part 33 and a side wall part 34. The fixed part 33 extends approximately along the entire length of the main body part 2 in the longitudinal direction on the side portion of the main body part 2. The fixed part 33 is fixedly attached to the side portion of the main body part 2. The fixation of the fixed part 33 and the main body part 2 may be achieved with an adhesive such as a hot-melt adhesive.

The side wall part 34 communicates with the inner side of the fixed part 33 in the width direction and extends together with the fixed part 33 in the longitudinal direction. The side wall part 34 is overlaid on the both side portions of the main body part 2 in the longitudinal direction and fixedly attached thereto with a hot-melt adhesive or the like. In the absorbent product 1, the pair of side wall parts 34 is provided on the side of the top sheet 21 in the vicinity of the both side portions of the absorbent core 4. The side-wall elastic member 32 extending in the longitudinal direction is joined in a stretched condition to the edge of each side wall part 34, i.e., free edge, with a hot-melt adhesive or the like. Each side-wall elastic member 32 includes at least one elastic element extending in the longitudinal direction. By the contraction of the side-wall elastic members 32, the side wall parts 34 stand toward the wearer and form standing gathers.

Examples of the aforementioned hot-melt adhesive that is used include a polyolefin-based adhesive, a rubber-based adhesive, and a vinyl acetate-based adhesive. The aforementioned joining such as the joining of the top sheet 21 and the back sheet 23 and the joining of the side sheets 3 and the main body part 2 may be achieved by, for example, heat fusion bonding or ultrasonic bonding. The joining of the side-wall elastic members 32 may be achieved by, for example, ultrasonic bonding.

The top sheet 21 may be formed of, for example, a liquid-pervious nonwoven fabric. The nonwoven fabric may be made of, for example, hydrophobic fiber (e.g., polypropylene, polyethylene, polyester, polyamide or nylon) whose surface has undergone hydrophilic treatment using a surfactant. The nonwoven fabric may also be made of hydrophilic fiber such as cellulose, rayon, or cotton. For example, the nonwoven fabric may be an air-through nonwoven fabric, a point-bonded nonwoven fabric, a spunbond nonwoven fabric, or a spunlace nonwoven fabric.

The back sheet 23 may be formed of, for example, a liquid-impervious or liquid-repellent nonwoven fabric made of hydrophobic fiber (e.g., a spunbond nonwoven fabric, a meltblown nonwoven fabric, or a spunbond-meltblown-spunbond (SMS) nonwoven fabric) or a liquid-impervious or liquid-repellent plastic film. The back sheet 23 may be a laminate of the nonwoven fabric and the plastic film. In the case where a plastic film is used for the back sheet 23, it is preferable that the plastic film has moisture permeability (i.e., air permeability) from the viewpoint of preventing the absorbent product 1 from becoming sweaty in order to improve the comfort of a wearer.

The side-sheet main bodies 31 may be formed of, for example, a liquid-impervious or liquid-repellent nonwoven fabric made of hydrophobic fiber (e.g., an air-through non-woven fabric, a point-bonded nonwoven fabric, a spunbond nonwoven fabric, a meltblown nonwoven fabric, or an SMS nonwoven fabric). As the elastic element of the side-wall elastic members 32, for example, polyurethane yarn, a strip-like polyurethane film, or filiform or strip-like natural rubber may be used. In the present embodiment, polyure-thane yarn is used as the elastic element.

Figure 3:
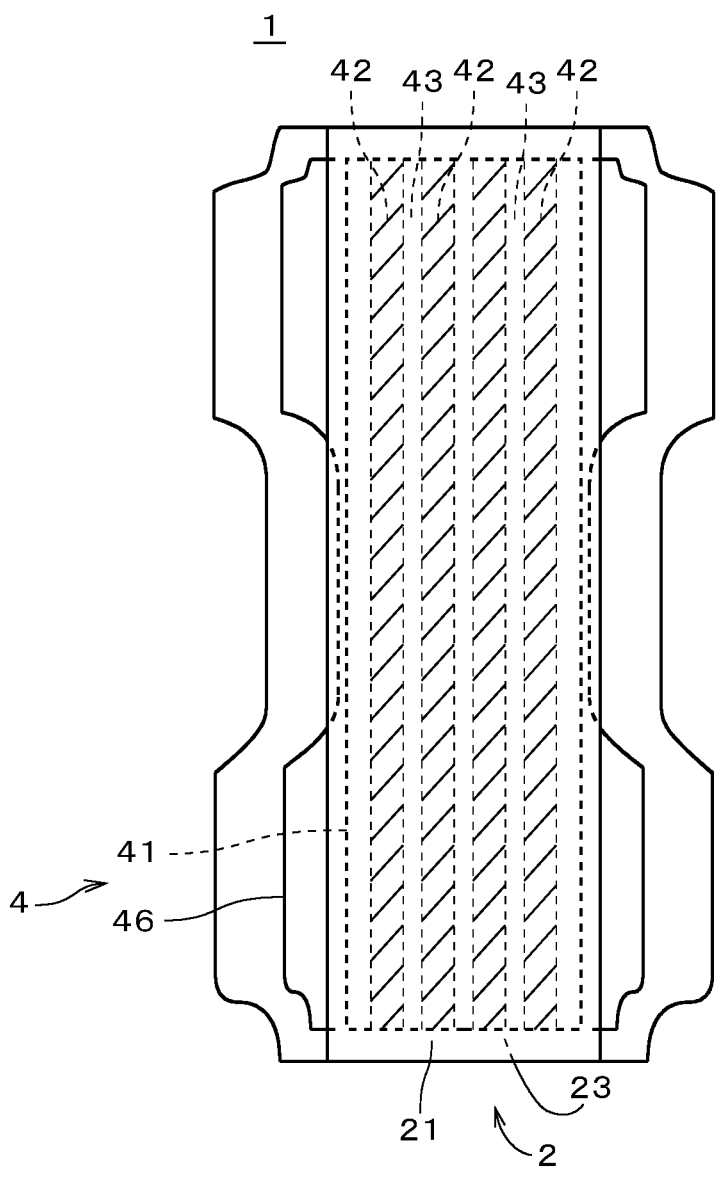
FIG. 3 is a plan view of a main body part.
Figure 4:
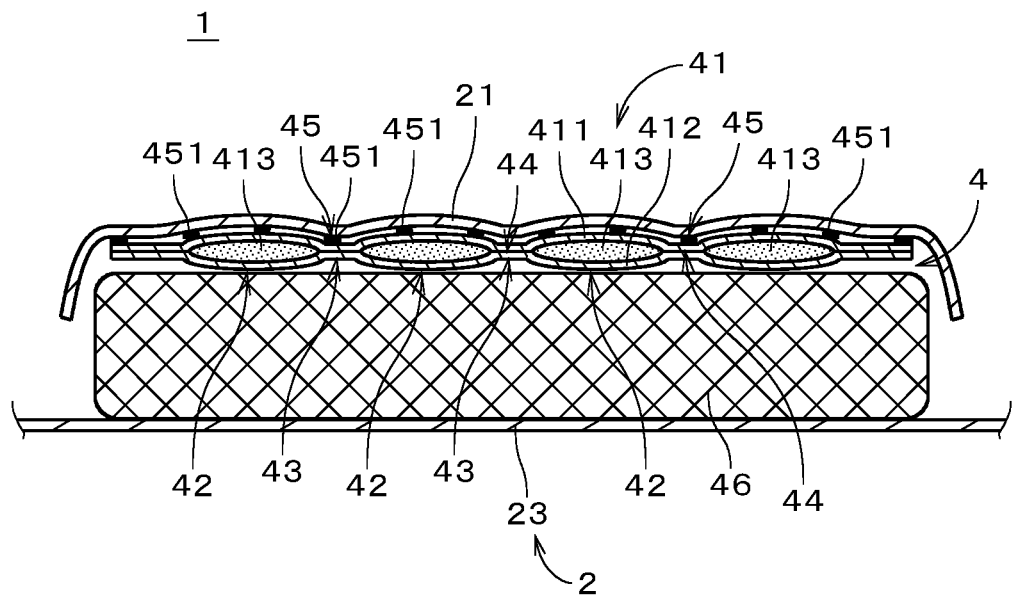
FIG. 4 is a sectional view of an absorbent core in enlarged dimensions.

FIG. 3 is a plan view illustrating the main body part 2 of the absorbent product 1. The side sheets 3 are not illustrated in FIG. 3. FIG. 4 is a sectional view illustrating the absorbent core 4 in FIG. 2 in enlarged dimensions. The absorbent core 4 includes an upper absorber 41 and a lower absorber 46. The upper absorber 41 is arranged on the upper side (wearer side) of the lower absorber 46. That is, the lower absorber 46 is arranged on the lower side (outer side) of the upper absorber 41. In FIG. 3, the outside shape of the upper absorber 41 is indicated by the broken line.

The lower absorber 46 includes a sheet-like fiber assem-bly. The lower absorber 46 is arranged between the upper absorber 41 and the back sheet 23 and joined to either or both of the upper absorber 41 and the back sheet 23. For example, the lower absorber 46 is larger in the width direction than the upper absorber 41 and has approximately the same size in the longitudinal direction as the upper absorber 41. The lower absorber 46 may be made of, for example, recycled hydrophilic fiber such as cellulose, rayon, or cotton, synthetic fiber, or pulp fiber. The lower absorber 46 may include a super absorbent material. Typically, the lower absorber 46 is wrapped around by, for example, tissue paper or a liquid-pervious nonwoven fabric. The shape of the lower absorber 46 is not limited to the example illus-trated in FIG. 3. For example, the lower absorber 46 may have a recess or the like extending in the longitudinal direction.

As illustrated in FIG. 4, the upper absorber 41 includes a liquid-pervious upper absorber sheet 411, a liquid-pervious lower absorber sheet 412, and a super absorbent material 413. The upper absorber sheet 411 is arranged on the side of the top sheet 21, and the lower absorber sheet 412 is arranged on the side of the back sheet 23 relative to the upper absorber sheet 411. The upper absorber 41 has an approxi-mately rectangular shape that is long in the longitudinal direction, and the upper absorber sheet 411 and the lower absorber sheet 412 are both shaped to extend in the longi-tudinal direction. The upper absorber sheet 411 and the lower absorber sheet 412 have approximately the same outside shape. The upper absorber 41 includes a plurality of material existence regions 42 to which the super absorbent material 413 is fixedly attached, and a plurality of material non-existence regions 43 in which the super absorbent material 413 does not exist. In FIG. 3, the material existence regions 42 are hatched.

The material existence regions 42, each having a strip shape extending in approximately parallel with the longitu-dinal direction, are arranged in the width direction with clearance therebetween (i.e., spaced from one another). In other words, the material existence regions 42 are arranged in strips extending in the longitudinal direction. In each material existence region 42, the super absorbent material

413 is arranged between the upper absorber sheet 411 and the lower absorber sheet 412 and fixedly attached to either or both of the upper absorber sheet 411 and the lower absorber sheet 412 with a hot-melt adhesive or the like. In other words, the super absorbent material 413 is fixedly attached to the material existence regions 42. In the example illustrated in FIGS. 3 and 4, the material existence regions 42 have approximately the same width, but they may have different widths.

The material non-existence regions 43 are regions of the upper absorber 41, excluding the material existence regions 42. The material non-existence regions 43 each have a strip shape extending in the longitudinal direction. In the example illustrated in FIGS. 3 and 4, the material non-existence regions 43 have the same width, but they may have different widths. For example, the width of the material non-existence regions 43 is smaller than the width of the material existence regions 42. The material non-existence regions 43 and the material existence regions 42 are alternately arranged in the width direction. That is, one material non-existence region 43 is provided between each pair of the material existence regions 42 that are adjacent to each other in the width direction. In FIG. 3, the boundaries between the material non-existence regions 43 and the material existence regions 42 are indicated by broken lines thinner than the broken line indicating the outside shape of the upper absorber 41.

Typically, in each material non-existence region 43, the super absorbent material 413 does not exist between the upper absorber sheet 411 and the lower absorber sheet 412. The super absorbent material 413 only needs to not sub-stantially exist, and a slight amount of the super absorbent material 413 may exist. In the material non-existence regions 43, the upper absorber sheet 411 and the lower absorber sheet 412 are joined together to form first joined portions 44. The first joined portions 44 are portions of the material non-existence regions 43 in which the upper absorber sheet 411 and the lower absorber sheet 412 are joined together. By way of one example, the first joined portions 44 may be formed by adhesive bonding using a hot-melt adhesive or the like. The adhesive bonding may be achieved by, for example, slot-die coating or curtain coating, and the adhesive may be applied to the entire of the material non-existence regions 43 between the upper absorber sheet 411 and the lower absorber sheet 412. Preferably, heat seal (heat fusion bonding) may also be performed in addition to the adhesive bonding. In this case, the first joined portions 44 are formed by complex bonding of the upper absorber sheet 411 and the lower absorber sheet 412. The complex bonding is, however, not an absolute necessity to form the first joined portions 44.

In the first joined portions 44, the upper absorber sheet 411 and the lower absorber sheet 412 are joined together throughout the material non-existence regions 43. Alterna-tively, the upper absorber sheet 411 and the lower absorber sheet 412 may not be joined in extremely small parts of the material non-existence regions 43. In the material non-existence regions 43, the ratio of the area of adhesion with the adhesive between the upper absorber sheet 411 and the lower absorber sheet 412 to the area of the material non-existence regions 43, i.e., the area ratio of a joint region in which the upper absorber sheet 411 and the lower absorber sheet 412 are joined together, in the material non-existence regions 43 may, for example, be 80% or higher, preferably 85% or higher, and more preferably 90% or higher. As described previously, the material non-existence regions 43 may be regions that slightly include the super absorbent material 413 (i.e., material low-density regions) or regions in which the density of the super absorbent material 413 is much lower than in the material existence regions 42.

Figure 5:
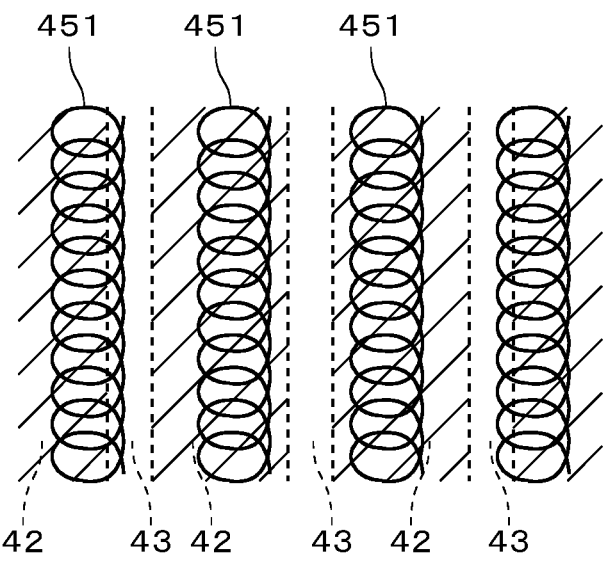
FIG. 5 is a diagram for describing joining of an upper absorber sheet and a top sheet.

The upper absorber sheet 411 is joined to the top sheet 21. The joining of the upper absorber sheet 411 and the top sheet 21 may be achieved by, for example, spiral coating illustrated in FIG. 5. In the spiral coating, spiral patterns each obtained by applying an adhesive 451 such as a hot-melt adhesive in spiral form in the longitudinal direction are arranged in width direction. Thus, the upper absorber sheet 411 and the top sheet 21 are partly joined together with the adhesive 451 as illustrated in FIG. 4. In the following description, portions of the material non-existence regions 43 in which the upper absorber sheet 411 and the top sheet 21 are joined together are referred to as "second joined portions 45." The second joined portions 45 are portions of the material non-existence regions 43 in which the upper absorber sheet 411 and the top sheet 21 are joined together. In the material non-existence regions 43 that include the second joined portions 45, the upper absorber sheet 411 and the top sheet 21 are partly joined together with the adhesive 451. In one example of the second joined portions 45, the adhesive 451 exists only in part of the material non-existence regions 43 in the width direction. In the second joined portions 45, the adhesive 451 may exist discretely in the longitudinal direction or the width direction.

The second joined portions 45 do not necessarily have to exist in all of the material non-existence regions 43. In the example illustrated in FIG. 4, in the material non-existence region 43 that is located in the center in the width direction, the top sheet 21 and the upper absorber sheet 411 are not joined together, and accordingly the second joined portion 45 does not exist. It goes without saying that the second joined portion 45 may be provided in the material non-existence region 43 located in the center (i.e., the second joined portions 45 may exist in all of the material non-existence regions 43), or in an arbitrary material non-existence region 43 other than the material non-existence region 43 located in the center, the top sheet 21 and the upper absorber sheet 411 may not be joined together. In the absorbent product 1, in at least one of the material non-existence regions 43, the top sheet 21 and the upper absorber sheet 411 are partly joined together to form the second joined portion 45.

In each material non-existence region 43 that includes the second joined portion 45, the ratio of the total area of the region to which the adhesive 451 adheres to the area of the material non-existence region 43, i.e., the area ratio of the joint region in which the upper absorber sheet 411 and the top sheet 21 are joined together, in the material non-existence region 43 may for example be 50% or lower, preferably 45% or lower, and more preferably 40% or lower. Accordingly, as will be described later, the top sheet 21 in the material non-existence region 43 is prone to being delaminated from the upper absorber sheet 411 when the super absorbent material 413 absorbs moisture and swells. The area ratio of the joint region may also be, for example, 1% or higher. During the manufacture of the absorbent product 1, it is preferable that the top sheet 21 and the upper absorber sheet 411 are joined together and are not misaligned from each other. From this viewpoint, the area ratio of the joint region may, for example, be 10% or higher, preferably 15% or higher, and more preferably 20% or higher.

As described previously, in the first joined portions 44, the upper absorber sheet 411 and the lower absorber sheet 412 are entirely joined together (in actuality, complex bonding is further performed), whereas in the second joined portions

45, the top sheet 21 and the upper absorber sheet 411 are partly joined together. Thus, in the case where a material non-existence region 43 is cut out from the absorbent product 1 and a peel test is conducted on each of the first joined portion 44 and the second joined portion 45, the load applied when the top sheet 21 and the upper absorber sheet 411 are delaminated and separated from each other in the second joined portion 45 is lower than the load applied when the upper absorber sheet 411 and the lower absorber sheet 412 are delaminated and separated from each other in the first joined portion 44. That is, the second joined portion 45 has lower peel strength than the first joined portion 44.

Similarly to the top sheet 21, the upper absorber sheet 411 and the lower absorber sheet 412 of the upper absorber 41 may also be formed of, for example, a liquid-pervious nonwoven fabric. The nonwoven fabric may be made of, for example, hydrophobic fiber (e.g., polypropylene, polyethylene, polyester, polyamide, or nylon) whose surface has undergone hydrophilic treatment using a surfactant. Alternatively, the nonwoven fabric may be made of hydrophilic fiber such as cellulose, rayon, or cotton. For example, the nonwoven fabric may be an air-through nonwoven fabric, a point-bonded nonwoven fabric, a spunbond nonwoven fabric, or a spunlace nonwoven fabric. As the super absorbent material 413, for example, granulated super absorbent polymer (SAP) or fibrous super absorbent fiber (SAF) may be used.

Here, comparison is made between the nonwoven fabric of the top sheet 21 and the nonwoven fabric of the upper absorber sheet 411. In the absorbent product 1, the fineness of the nonwoven fabric of the top sheet 21 is higher than the fineness of the nonwoven fabric of the upper absorber sheet 411. By way of one example, the nonwoven fabric of the top sheet 21 has fineness higher than or equal to 4.4 dtex. The fineness of the nonwoven fabric of the top sheet 21 may, for example, be 1.1. times or more of the fineness of the nonwoven fabric of the upper absorber sheet 411 and preferably 1.5 times or more. There are no particular limitations on the upper limit for the fineness of the nonwoven fabric of the top sheet 21, the upper limit may, for example, be 3.5 times or preferably 3.0 times. The basic weight of the nonwoven fabric of the top sheet 21 is greater than the basic weight of the nonwoven fabric of the upper absorber sheet 411. By way of one example, the nonwoven fabric of the top sheet 21 may have a basic weight greater than or equal to 25 g/m². The basic weight of the nonwoven fabric of the top sheet 21 may, for example, be 1.1 times or more of the basic weight of the nonwoven fabric of the upper absorber sheet 411 and preferably 1.2 times or more. There are no particular limitations on the upper limit for the basic weight of the nonwoven fabric of the top sheet 21, the upper limit may, for example, be 2.5 times and preferably 2.0 times.

In one example of the absorbent product 1, the fiber orientation of the nonwoven fabric of the top sheet 21 (typically, the longitudinal direction of the nonwoven fabric taken out from a roll) is approximately parallel to the longitudinal direction of the main body part 2, and the fiber orientation of the nonwoven fabric of the upper absorber sheet 411 is also approximately parallel to the longitudinal direction of the main body part 2. Thus, the nonwoven fabric of the top sheet 21 and the nonwoven fabric of the upper absorber sheet 411 are both less prone to being stretched in a direction corresponding to the longitudinal direction of the main body part 2 (hereinafter, simply referred to as the "longitudinal direction").

In a tensile test described later, the load applied when the nonwoven fabric of the top sheet 21 is stretched 3% in a direction corresponding to the width direction of the main body part 2 (hereinafter, simply referred to as the "width direction"), the load being hereinafter simply referred to as the "3% stretching load," is twice or more of the 3% stretching load of the nonwoven fabric of the upper absorber sheet 411 in the width direction. The 3% stretching load of the top sheet 21 in the width direction may preferably be 2.2 times or more of the 3% stretching load of the upper absorber sheet 411. There are no particular limitations on the 3% stretching load of the top sheet 21, the upper limit may, for example, be 10.0 times. As described above, the top sheet 21 is less prone to being stretched in the width direction as compared with the upper absorber sheet 411. In other words, the upper absorber sheet 411 is more prone to being stretched in the width direction than the top sheet 21. In actuality, the lower absorber sheet 412 is also similarly more prone to being stretched in the width direction than the top sheet 21.

Figure 6:
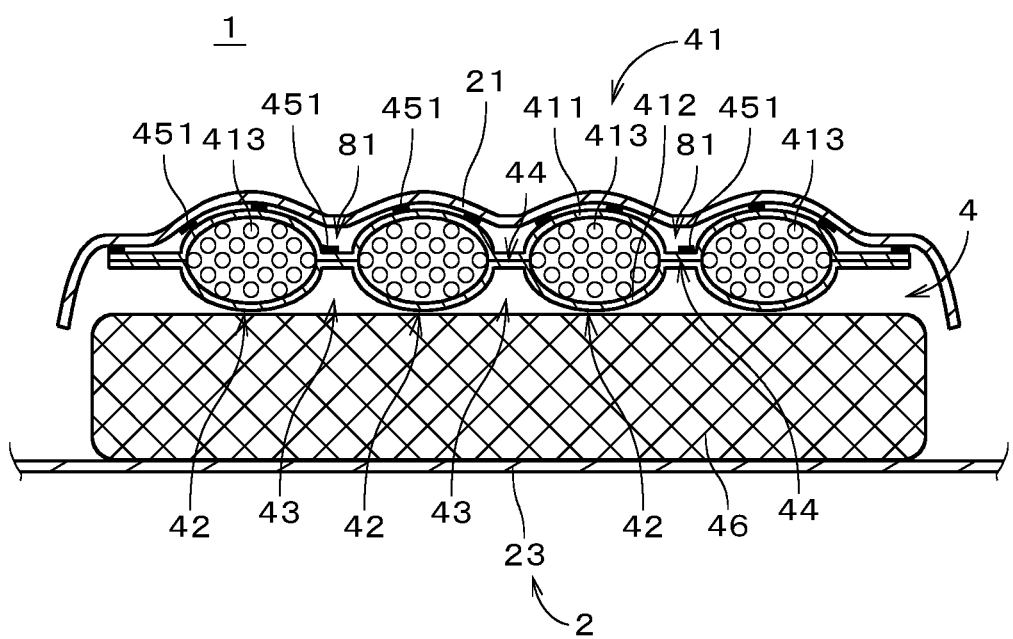
FIG. 6 is a sectional view of the absorbent core with a swelling super absorbent material.

In the absorbent product 1, when body waste such as urine is discharged from the wearer, part of moisture that reaches the absorbent core 4 through the top sheet 21 is guided to the lower absorber 46 through the material non-existence regions 43 and absorbed by the lower absorber 46. The other part of the moisture is absorbed by the super absorbent material 413 in the material existence regions 42 of the upper absorber 41, so that the super absorbent material 413 swells as illustrated in FIG. 6. FIG. 6 shows a state in which a relatively large amount of moisture is absorbed by the super absorbent material 413.

At this time, since the upper absorber sheet 411 and the lower absorber sheet 412 are prone to being stretched in the width direction, the upper absorber sheet 411 and the lower absorber sheet 412 in the material existence regions 42 become deformed in accordance with the swelling of the super absorbent material 413. In the material non-existence regions 43, the joining of the upper absorber sheet 411 and the lower absorber sheet 412 (first joined portion 44) is more or less maintained.

On the other hand, the top sheet 21 is less prone to being stretched in the width direction. Thus, in the material non-existence regions 43 including the second joined portions 45 (see FIG. 4), when the rate of swelling of the super absorbent material 413 (the amount of absorption) increases in the adjacent material existence regions 42, the top sheet 21 does not follow the deformation of the super absorbent material 413, and accordingly the top sheet 21 in the material non-existence regions 43 is delaminated from the upper absorber sheet 411. That is, the second joined portions 45 are separated. This produces spaces 81 (hereinafter, referred to as the "delamination spaces 81") between the top sheet 21 and the upper absorber sheet 411 in the material non-existence regions 43. In actuality, the top sheet 21 and the upper absorber sheet 411 are not delaminated entirely along the entire material non-existence region 43 in the longitudinal direction, and the delamination occurs in regions where the rate of swelling of the super absorbent material 413 is high in adjacent material existence regions 42.

In the absorbent product 1, the presence of the delamination spaces 81 accelerates the diffusion of moisture in the longitudinal direction and allows a wide area of the absorbent core 4 to be used for the absorption of moisture. Besides, even if moisture seeps out from the lower absorber 46 due to, for example, body pressure applied from the wearer, the moisture is retained in the delamination spaces 81, and this suppresses the seeping out of the moisture to the surface of the top sheet 21 on the wearer side (i.e., fluid return). From the viewpoint of improving liquid diffusion properties and suppressing fluid return, the delamination of the top sheet 21 and the upper absorber sheet 411 in the material non-existence regions 43 may occur only in at least part of the area in the longitudinal direction. In the case where there is a material non-existence region 43 that includes no second joined portion 45 (i.e., the top sheet 21 and the upper absorber sheet 411 are not joined together), a space similar to the delamination space 81 is also formed between the top sheet 21 and the upper absorber sheet 411 in this material non-existence region 43.

Next, experimental examples of the absorbent product 1 will be described. First, tensile characteristics of the top sheet 21 and the upper absorber sheet 411 were measured. In the measurement of the tensile characteristics, a nonwoven fabric for forming the top sheet 21 of the absorbent product 1 and a nonwoven fabric for forming the upper absorber sheet 411 were prepared. Also, a nonwoven fabric for forming a top sheet used in a conventional absorbent product (hereinafter, referred to as the "top sheet of the comparative example") was prepared. The nonwoven fabric of the top sheet 21 had fineness of 4.4 dtex, the nonwoven fabric of the upper absorber sheet 411 had fineness of 2.0 dtex, and the nonwoven fabric of the top sheet of the comparative example had fineness of 2.2 dtex. The basic weight of the nonwoven fabric of the top sheet 21 was 25 g/m², the basic weight of the nonwoven fabric of the upper absorber sheet 411 was 17 g/m², and the basic weight of the nonwoven fabric of the top sheet of the comparative example was 18 g/m². Note that the fineness and basic weight of each of the top sheet 21 and the upper absorber sheet 411 of the absorbent product 1 are not limited to the examples described above. Then, a tensile test was conducted on each of the longitudinal direction and the width direction of each nonwoven fabric in conformity with JIS L1913 6.3.1 to measure the 3% stretching load, tensile strength, and tensile elongation as the tensile characteristics. Table 1 shows the results of measurement of the tensile characteristics.

TABLE 1

| | Item | | | | | |
|---|---|---|---|---|---|---|
| | 3% Stretching Load [%] | | Tensile Strength [N/50 mm] | | Tensile Elongation [%] | |
| | | | Direction | | | |
| Test Piece | Longitudinal | Width | Longitudinal | Width | Longitudinal | Width |
| Top Sheet | 7.00 | 0.36 | 52.08 | 13.99 | 43.58 | 102.54 |
| Upper Absorber Sheet | 8.24 | 0.15 | 44.98 | 6.16 | 22.67 | 88.94 |
| Top Sheet of Comparative Example | 6.25 | 0.27 | 45.42 | 6.68 | 26.60 | 60.11 |

As described previously, the longitudinal direction is approximately parallel to the fiber orientation of the nonwoven fabric (typically, the longitudinal direction of the nonwoven fabric taken out from a roll), and the width direction is approximately perpendicular to the fiber orientation of the nonwoven fabric. The 3% stretching load is the load applied when the nonwoven fabric is stretched 3% in each direction, using a length of the test piece before test as a reference. As the 3% stretching load of the nonwoven fabric in each direction increases, a greater force becomes necessary to stretch the nonwoven fabric 3% from the reference length, and it can be said that the nonwoven fabric is less prone to being stretched in that direction. The tensile strength is the value obtained by dividing the load applied when the test piece is stretched until rupture in the tensile test by the width of the test piece (50 mm). The tensile elongation is the elongation percentage of the test piece until rupture of the test piece in the tensile test.

Focusing only on the width direction, the nonwoven fabric of the top sheet 21 is superior in all characteristics including the 3% stretching load, the tensile strength, and the tensile elongation to the nonwoven fabric of the upper absorber sheet 411 and the nonwoven fabric of the top sheet of the comparative example. To be more specific, the 3% stretching load of the nonwoven fabric of the top sheet 21 in the width direction is greater than the 3% stretching load of the nonwoven fabric of the top sheet of the comparative example, and is twice or more of the 3% stretching load of the nonwoven fabric of the upper absorber sheet 411. Thus, the top sheet 21 is less prone to being stretched in the width direction as compared with the top sheet of the comparative example, and is much less prone to being stretched as compared with the upper absorber sheet 411. Also, the tensile strength of the nonwoven fabric of the top sheet 21 in the width direction is much higher than the tensile strength of the nonwoven fabric of the upper absorber sheet 411 and the tensile strength of the nonwoven fabric of the top sheet of the comparative example (in actually, twice or more).

Next, absorption characteristics of the absorbent product 1 were measured. In the measurement of the absorption characteristics, an absorbent product that replaced the top sheet 21 of the absorbent product 1 by the top sheet of the comparative example (hereinafter, referred to as the "absorbent product of the comparative example") was prepared, in addition to the absorbent product 1. Then, absorption velocity and the amount of fluid return were measured as the absorption characteristics for each of the absorbent product 1 and the absorbent product of the comparative example. Table 2 shows the results of measurement of the absorption characteristics.

In the measurement of the absorption velocity, a ring for measuring absorption velocity (with an inside diameter of 25 mm, a height of 200 mm, and a weight of 1293 g) was set on the center of an absorbent product to be measured, 150 ml of a saline solution (common salt concentration of 1.0%) was poured on the absorbent product, and time was calculated from the start of pouring until the end of absorption of the saline solution to obtain the time of absorption (seconds). After the absorbent product was left alone for 10 minutes, the second pouring of the saline solution was conducted to obtain the absorption time. Then, after the absorbent product was further left alone for 10 minutes, the third pouring of the saline solution was conducted to obtain the absorption time.

In the measurement of the amount of fluid return, 150 cc of a saline solution (common salt concentration of 1.0%) was vertically poured without stopping on around the center of the groin portion of the absorbent product, using a separating funnel. At this time, the vertical distance from the dropping end of the separating funnel to the top sheet of the absorbent product was set to be 5 cm. Simultaneously with the start of pouring, time was started to be calculated, and after a lapse of 5 minutes, 25 pieces of filter paper with a diameter of 110 mm were placed on the receiving portion of the absorbent product. Then, a 3.5-kg weight was placed on the receiving portion of the absorbent product for 30 seconds, and the amount of fluid return (g) was measured on the basis of a difference in the weight of the filter paper before and after the test. Moreover, after a lapse of 10 minutes since the start of the first pouring, 150 cc of a new saline solution was poured without stopping on the same portion of the absorbent product as in the first pouring. Then, after a lapse of 5 minutes since the start of the second pouring, 25 pieces of new filter paper were placed on the absorbent product. After a lapse of 5 minutes and 30 seconds since the start of the second pouring, the amount of fluid return was measured (second measurement) in the same manner as in the first measurement. Similarly to the first measurement and the second measurement, the third measurement of the amount of fluid return was conducted.

Focusing on the absorption velocity, although in the first measurement, the absorption time of the absorbent product 1 was almost the same as the absorption time of the absorbent product of the comparative example, in the second and third measurements, the absorption time of the absorbent product 1 was considerably shorter than the absorption time of the absorbent product of the comparative example. In other words, in the second and third measurements, the absorption velocity of the absorbent product 1 was higher than the absorption velocity of the absorbent product of the comparative example.

TABLE 2

| Test Piece | Item | | | | | |
| | First | | Second | | Third | |
| | Amount of Fluid Return [g] | Absorption Time [sec] | Amount of Fluid Return [g] | Absorption Time [sec] | Amount of Fluid Return [g] | Absorption Time [sec] |
|---|---|---|---|---|---|---|
| Absorbent Product | 0.02 | 29.6 | 0.25 | 22.5 | 4.18 | 19.4 |
| Absorbent Product of Comparative Example | 0.04 | 28.8 | 0.57 | 25.6 | 5.95 | 26.5 |

Focusing on the amount of fluid return, although in the first measurement, the amount of fluid return in the absorbent product 1 was almost the same as the amount of fluid return in the absorbent product of the comparative example, in the second and third measurements, the amount of fluid return in the absorbent product 1 was considerably smaller than the amount of fluid return in the absorbent product of the comparative example. In this way, the absorbent product 1 suppresses the return of moisture from the absorbent core 4 to the wearer side of the top sheet as compared with the absorbent product of the comparative example.

In the measurement of the absorption characteristics, the reason why the absorbent product 1 had a higher absorption velocity and a reduced amount of fluid return (i.e., had improved absorption characteristics) are not obvious, but it can be considered that, in the absorbent product 1, the delamination spaces 81 formed by the delamination of the top sheet 21 and the upper absorber sheet 411 in the material non-existence regions 43 contribute to the improvement in the absorption characteristics.

As described above, in the absorbent product 1, the absorbent core 4 includes the upper absorber 41 in which the super absorbent material 413 is fixedly attached between the upper absorber sheet 411 and the lower absorber sheet 412, and the lower absorber 46 that includes the sheet-like fiber assembly. In the upper absorber 41, the material existence regions 42 to which the super absorbent material 413 is fixedly attached are arranged in the width direction with clearance therebetween, and a material non-existence region 43 in which the super absorbent material 413 does not exist is arranged between each pair of the material existence regions 42 that are adjacent to each other in the width direction. In each material non-existence region 43, the upper absorber sheet 411 and the lower absorber sheet 412 are entirely joined together to form the first joined portion 44. In at least one material non-existence region 43, the top sheet 21 and the upper absorber sheet 411 are partly joined together to form the second joined portion 45. Then, the load applied when the nonwoven fabric of the top sheet 21 is stretched 3% in the width direction is twice or more of the load applied when the nonwoven fabric of the upper absorber sheet 411 is stretched 3% in the width direction.

In the absorbent product 1, the top sheet 21 in the material non-existence regions 43 is delaminated from the upper absorber sheet 411 due to the swelling of the super absorbent material 413, and the delamination spaces 81 are formed between the top sheet 21 and the upper absorber sheet 411. As a result, the presence of the delamination spaces 81 improves liquid diffusion properties and suppresses fluid return. This also prevents the top sheet 21 in the material non-existence regions 43 to become recessed deeply toward the absorbent core 4, and accordingly suppresses a decrease in wearing comfort.

Preferably, the tensile strength of the nonwoven fabric of the top sheet 21 in the width direction may be higher than the tensile strength of the nonwoven fabric of the upper absorber sheet 411. In this case, it is possible to appropriately form the delamination spaces 81 without rupture of the top sheet 21 and to more reliably improve liquid diffusion properties and suppress fluid return.

Preferably, the fineness of the nonwoven fabric of the top sheet 21 may be 1.1 times or more of the fineness of the nonwoven fabric of the upper absorber sheet 411. When the top sheet 21 has high fineness in this way, the surface area of fiber of the top sheet 21 to which the adhesive adheres becomes smaller than that of the upper absorber sheet 411.

This allows the top sheet 21 in the material non-existence regions 43 to be easily delaminated from the upper absorber sheet 411.

Preferably, the basic weight of the nonwoven fabric of the top sheet 21 may be 1.1 times or more of the basic weight of the nonwoven fabric of the upper absorber sheet 411. The great basic weight of the top sheet 21 allows the top sheet 21 to have higher stiffness than the upper absorber sheet 411 and allows the top sheet 21 in the material non-existence regions 43 to be easily delaminated from the upper absorber sheet 411.

Preferably, in the material non-existence region 43 including the second joined portion 45, the joint region in which the top sheet 21 and the upper absorber sheet 411 are joined together may have an area ratio higher than or equal to 1% and lower than or equal to 50%. In this case, the swelling of the super absorbent material 413 easily causes the delamination of the top sheet 21 and forms the delamination space 81. Moreover, since the second joined portion 45 has lower peel strength than the first joined portion 44, the delamination of the top sheet 21 occurs with more reliability.

The absorbent product 1 described above may be modified in various ways.

The tensile strength of the nonwoven fabric of the top sheet 21 in the width direction may be lower than or equal to the tensile strength of the nonwoven fabric of the upper absorber sheet 411 as long as the 3% stretching load of the nonwoven fabric of the top sheet 21 in the width direction is twice or more of the 3% stretching load of the nonwoven fabric of the upper absorber sheet 411. Similarly, the fineness of the nonwoven fabric of the top sheet 21 may be lower than 1.1 times of the fineness of the nonwoven fabric of the upper absorber sheet 411, or the basic weight of the nonwoven fabric of the top sheet 21 may be lower than 1.1 times of the basic weight of the nonwoven fabric of the upper absorber sheet 411.

The area ratio of the joint region of the top sheet 21 and the upper absorber sheet 411 in the material non-existence regions 43 may be higher than 50% as long as the delamination spaces 81 can be formed between the top sheet 21 and the upper absorber sheet 411 by the swelling of the super absorbent material 413. Moreover, the peel strength of the second joined portion 45 may be higher than or equal to the peel strength of the first joined portion 44.

The joining of the upper absorber sheet 411 and the lower absorber sheet 412 in the first joined portions 44 may be achieved by any method other than adhesive bonding. Similarly, the joining of the top sheet 21 and the upper absorber sheet 411 in the second joined portions 45 may be achieved by any method other than adhesive bonding.

The number and shape of the material existence regions 42 provided in the absorbent core 4 may be modified in various ways. The material non-existence regions 43 may have any shape other than the linear shape, and for example, may spread out continuously in mesh-like form in the longitudinal direction.

The side sheets 3 may be omitted from the absorbent product 1. The structure of the absorbent product 1 described above may be used for absorbent products other than auxiliary absorbent pads, such as pant-like or taped disposable diapers.

The configurations of the preferred embodiments and variations described above may be appropriately combined as long as there are no mutual inconsistencies.

While the invention has been shown and described in detail, the foregoing description is in all aspects illustrative and not restrictive. It is therefore to be understood that numerous modifications and variations can be devised without departing from the scope of the invention.

REFERENCE SIGNS LIST

1 absorbent product
4 absorbent core
21 top sheet
23 back sheet
41 upper absorber
42 material existence region
43 material non-existence region
44 first joined portion
45 second joined portion
46 lower absorber
411 upper absorber sheet
412 lower absorber sheet
413 super absorbent material

The invention claimed is:

1. An absorbent product for receiving body waste from a wearer, the absorbent product comprising:

a liquid-pervious top sheet;

a water-repellent or liquid-impervious back sheet; and an absorbent core disposed between said top sheet and said back sheet and extending in a longitudinal direction, wherein said absorbent core includes:

an upper absorber including a super absorbent material fixedly attached between an upper absorber sheet and a lower absorber sheet; and a lower absorber including a fiber assembly and disposed between said upper absorber and said back sheet, said upper absorber includes a plurality of material existence regions that are arranged in a width direction with clearance therebetween and to which said super absorbent material is fixedly attached, and a plurality of material non-existence regions in which said super absorbent material does not exist, each material non-existence region being arranged between a respective pair of said plurality of material existence regions that are adjacent to each other in said width direction, in each material non-existence region, said upper absorber sheet and said lower absorber sheet are entirely joined together using heat fusion bonding to form a first joined portion, between said top sheet and said upper absorber sheet, patterns each obtained by applying an adhesive in said longitudinal direction are arranged in said width direction to partly join said top sheet and said upper absorber sheet, such that in at least one first material non-existence region of the plurality of material non-existence regions, said top sheet and said upper absorber sheet are partly joined together to form a second joined portion, a load applied when nonwoven fabric of said top sheet is stretched 3% in said width direction is twice or more of a load applied when nonwoven fabric of said upper absorber sheet is stretched 3% in said width direction, and in the at least one first material non-existence region, said top sheet is configured to, when said super absorbent material swells, delaminate from said upper absorber sheet to form a delamination space between said top sheet and said upper absorber sheet in the at least one first material non-existence region while said first joined portion is maintained throughout said absorbent core in the at least one first material non-existence region.

2. The absorbent product according to claim 1, wherein the nonwoven fabric of said top sheet has higher tensile strength in said width direction than the nonwoven fabric of said upper absorber sheet.

3. The absorbent product according to claim 1, wherein fineness of the nonwoven fabric of said top sheet is 1.1 times or more of fineness of the nonwoven fabric of said upper absorber sheet.

4. The absorbent product according to claim 1, wherein a basis weight of the nonwoven fabric of said top sheet is 1.1 times or more of a basis weight of the nonwoven fabric of said upper absorber sheet.

5. The absorbent product according to claim 1, wherein in the at least one first material non-existence region including said second joined portion, a joint region in which said top sheet and said upper absorber sheet are joined together has an area ratio higher than or equal to 1% and lower than or equal to 50%.

6. The absorbent product according to claim 1, wherein said second joined portion has lower peel strength than said first joined portion.

7. The absorbent product according to claim 1, wherein in at least one second material non-existence region of the plurality of material non-existence regions, said top sheet and said upper absorber sheet are not joined together.

* * * * *